United States Patent [19] [11] Patent Number: 4,835,302
Kato et al. [45] Date of Patent: May 30, 1989

[54] METHOD FOR PRODUCING INDAN DERIVATIVES

[75] Inventors: Takeshi Kato; Tomoyuki Fujii, both of Osaka, Japan

[73] Assignee: Takeda Chemical Industries, Ltd., Japan

[21] Appl. No.: 162,639

[22] Filed: Mar. 1, 1988

[30] Foreign Application Priority Data

Mar. 4, 1987 [JP] Japan ................................. 62-50876

[51] Int. Cl.$^4$ .......................................... C07C 103/52
[52] U.S. Cl. ....................................................... 560/41
[58] Field of Search .......................................... 560/41

[56] References Cited

U.S. PATENT DOCUMENTS 4,532,342 7/1985 Hoefle et al. ......................... 560/38

FOREIGN PATENT DOCUMENTS 0051391 5/1982 European Pat. Off. .
2095682 10/1982 United Kingdom .

OTHER PUBLICATIONS

Chemical and Pharmaceutical Bulletin, Miyake et al., vol. 34, No. 7, 1986, pp. 2852–2858, (English).

Chemische Berichte, Cosmatos et al., vol. 94, No. 10, 1961, pp. 2644–2655, (German).

The Journal of Synthetic Organic Chemistry, Shioiri et al, vol. 31, No. 8, 1973, pp. 666–674, (Japanese).

Primary Examiner—Bruce D. Gray
Attorney, Agent, or Firm—Wegner & Bretschneider

[57] ABSTRACT

A method for producing an indan derivative represented by the formula:

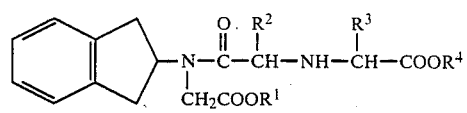

by condensing an N-(α-alkoxycarbonylaralkyl)-α-amino acid with an N-(indan-2-yl)glycine alkyl or aralkyl ester in the presence of a diphenyl phosphorochloridate, and a method for producing another indan derivative having anti-hypertensive activity by using the above intermediate indan derivative are useful for industrial production of the indan derivative having anti-hypertensive activity.

44 Claims, No Drawings

METHOD FOR PRODUCING INDAN DERIVATIVES

INDUSTRIAL FIELD OF UTILIZATION

This invention relates to a method for producing indan derivatives having antihypertensive activities due to angiotensin converting enzyme (ACE) inhibitory activities, and a method for producing intermediates for producing them.

BACKGROUND OF THE INVENTION

As the compounds exhibiting antihypertensive activities due to ACE inhibitory activities, there are known indan derivatives represented by the formula

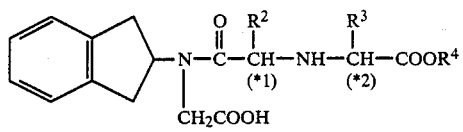

[wherein $R^2$ stands for a lower alkyl group (preferably methyl group), $R^3$ stands for an aralkyl group (preferably phenethyl group) and $R^4$ stands for a lower alkyl group (preferably ethyl group), and the asymmetric carbon atoms designated (*1) and (*2) are both desirably in (S)-configuration] and salts (preferably hydrochloride) thereof [Japanese Unexamined Patent Publication No. 57-77651; Japanese Unexamined Patent Publication No. 57-179141; Chem. Pharm. Bull, 34, pp. 2852 (1986)].

In Japanese Unexamined Patent Publication No. 57-77651 and Japanese Unexamined Patent Publication No. 57-179141, the following method is described as a typical one for preparing the compound (Ia).

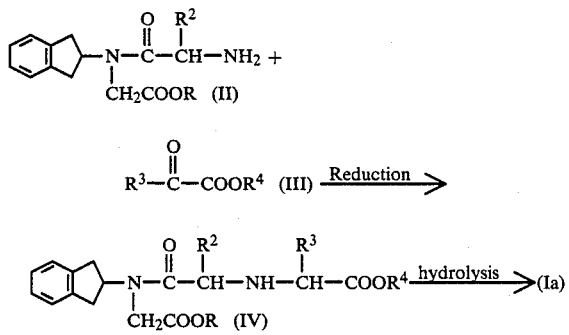

(Upon necessity)
[wherein R stands for hydrogen or a lower alkyl group]

In the above method, the compound (Ia) is usually obtained as a mixture of two kinds of steric isomers (asymmetric carbon of *2). Therefore, for obtaining a desired optically-active compound, it is necessary to resort to, for example, optical resolution.

In Chemical and Pharmaceutical Bulletin, 34, p. 2852 (1986), the following method is described.

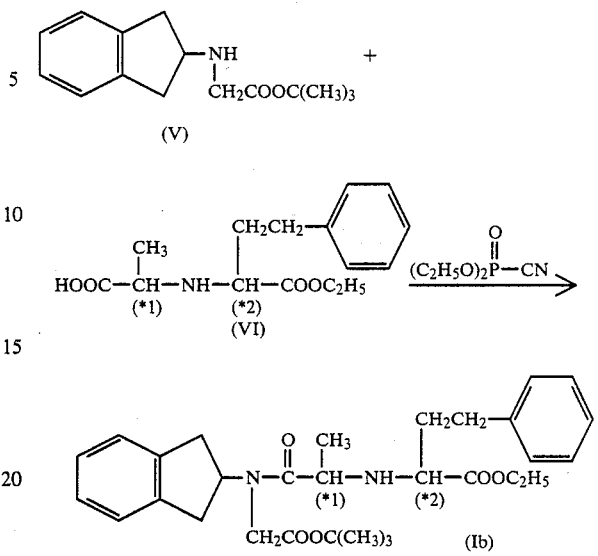

The above method comprises condensation of the compound (V) with (VI) in the presence of diethyl phosphorocyanidate (DEPC). This method has some problems from the industrial viewpoint in that highly toxic DEPC is used, and that hydrogen cyanide is generated by the hydrolysis of DEPC and further that the yield is not high (yield: 68%).

And, in Japanese Unexamined Patent Publication No. 57-176941, the following method is described.

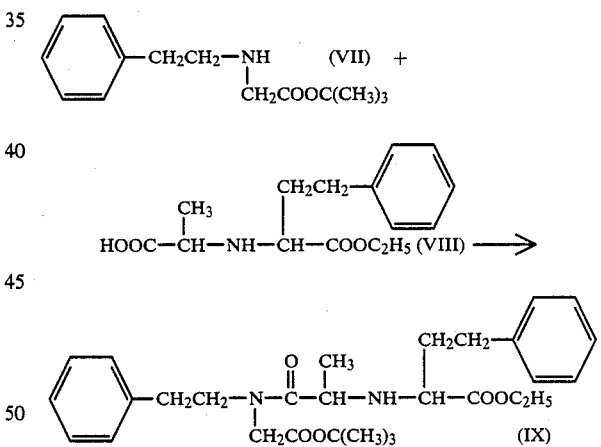

The above reaction yields the compound (IX) by allowing the compound (VII) to react with an acyl derivative of the acid represented by the formula (VIII) under amide-forming conditions. This method also has some problems from the industrial viewpoint in that use of an acyl derivative of the compound of the formula (VIII) is required and that the yield is not high (yield: 69.7%).

DETAILED DESCRIPTION OF THE INVENTION

The present inventors diligently studied industrial methods of preparing the compound (Ia), and found that use of diphenyl phosphorochloridate derivatives known as materials of a mixed acid anhydride for activating a carboxyl group in the case of a peptide synthesis [Chem. Ber., 94, p. 2644 (1961)] served to condense a compound represented by the formula

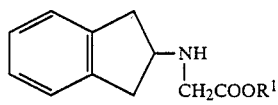

[wherein $R^1$ stands for a lower alkyl group or an aralkyl group] directly with a compound represented by the formula

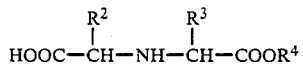

[wherein $R^2$ stands for a lower alkyl group, $R^3$ stands for an aralkyl group and $R^4$ stands for a lower alkyl group], to produce a compound represented by the formula

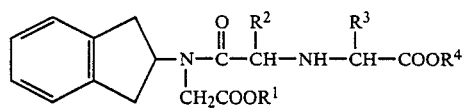

[wherein each of the symbols is of the same meaning as defined above] in a high yield.

Further surprisingly, the present inventors found that the compound (I) was also obtained in a high yield even by mixing the compound (XI) and a diphenyl phosphorochloridate derivative and then adding the compound (XII) to the mixture. This fact shows that the condensation reaction employing a diphenyl phosphorochloridate derivative does not proceed through such a mixed acid anhydride of the compound (VI) as reported in Chemishe Berichte, 94, p. 2644 (1961) nor through an acyl derivative of the compound (VI) as described in Japanese Unexamined Patent Publication No. 57-176941. Namely, the present inventors found that a diphenyl phosphorochloridate derivative was a new type of condensing agent and have completed the present invention.

More specifically, the present invention provides a method for producing the compound represented by the formula (I), which is characterized by allowing a diphenyl phosphorochloridate derivative represented by the formula

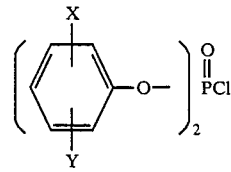

[wherein X and Y independently stand for hydrogen, a lower alkyl group, a lower alkoxy group or halogen] and the compound represented by the formula (XII) to react with the compound represented by the formula (XI), and a method for producing the compound represented by the formula (Ia) or the salt thereof, which is characterized by subjecting the compound represented by the formula (I) which is obtained by the above-mentioned method to a hydrolysis, elimination of catalytic reduction reaction.

Referring to the above formulae, the lower alkyl groups shown by $R^1$, $R^2$, $R^4$, X and Y are exemplified by alkyl groups having about 1 to 4 carbon atoms such as methyl, ethyl, propyl, isobutyl, sec-butyl and tert-butyl. As $R^2$, a methyl group is preferable, and, as $R^4$, an ethyl group is preferable.

Examples of the aralkyl group shown by $R^1$ include phenyl-lower($C_{1-4}$)alkyl groups and diphenyl-lower($C_{1-4}$)alkyl groups such as benzyl, phenethyl and diphenylmethyl. The phenyl moiety of the phenyl-lower alkyl group and diphenyl-lower alkyl group may optionally have 1 to 3 substituents such as a lower($C_{1-4}$)alkyl group (e.g. methyl, ethyl, propyl), a lower($C_{1-4}$)alkoxy group (e.g. methoxy, ethoxy, propoxy, isopropoxy) and halogen (e.g. fluorine, chlorine, bromine).

Examples of the aralkyl group shown by $R^3$ include phenyl-lower($C_{1-4}$)alkyl groups such as benzyl, phenethyl and 3-phenylpropyl, and, among them, phenethyl group is preferable.

Examples of the alkoxy group shown by X and Y include alkoxy groups having 1 to 4 carbon atoms, such as methoxy, ethoxy, propoxy, isopropoxy and butoxy.

The halogen shown by X and Y is exemplified by fluorine, chlorine and bromine.

As $R^1$, tert-butyl group or benzyl is preferable (more preferably benzyl group), and, as X and Y, hydrogen is preferably, As the compound (XII), N-[(S)-1-ethoxycarbonyl-3-phenylpropyl]-L-alanine is preferable.

The above reaction of the compounds (XI), (XII) and (XIII) is usually conducted in a solvent in the presence of a base. As the base to be used, tertiary amines which are inert to the reaction (e.g. triethylamine, N-methylpiperidine, dimethylaniline, pyridine, 4-dimethylaminopyridine) are preferable, and triethylamine is more preferable. As the solvent, any one which is inert to the reaction may be employed, but organic solvents having relatively low boiling points, such as methylene chloride, ethyl acetate, chloroform, tetrachloroethane and tetrahydrofuran are preferable. The above bases can also be used as solvents. The reaction temperature usually ranges from $-20°$ C. to $+50°$ C., preferably from $-5°$ C. to $+30°$ C. Amounts of the compound (XI), the compound (XIII) and the base to be employed are not specifically limited, but it is economically efficient to use, relative to the compound (XII), generally 1.0 to 1.5 equivalents of the compound (XI), 1.0 to 2.0 equivalents of the compound (XIII) and 1 to 4 equivalents of the base. The reaction time is not specifically limited, but, in the case of condensing the compound (XI) with the compound (XII) in the presence of the compound (XIII), it is preferably 0.5 to 5 hours.

After the compounds (XI) and (XIII) are mixed in a solvent in the presence of a base, the compound (XII) may be added to the reaction mixture. The kinds and amounts of the bases and the solvents to be employed are the same as those mentioned above. The period for stirring the compounds (XI) and (XIII) in the solvent is not specifically limited, but a period ranging from 1 to 20 hours is generally preferable. Isolation and purification of the compound (I) from the reaction mixture can be conducted by conventional means (e.g. extraction, concentration, column chromatography).

The compound (XI) can be synthesized by, for example, the methods described in Japanese Unexamined Patent Publication No. 57-77651; Japanese Unexamined Patent Publication No. 57-179141; and Chemical and Pharmaceutical Bulletin, 34, p. 2852 (1986).

The compound (XII) can be synthesized by, for example, the methods described in Japanese Unexamined Patent Publication No. 58-103364; Japanese Unexamined Patent Publication No. 67-178954; and Chemical and Pharmaceutical Bulletin 34, p. 2852 (1986).

The compound (XIII) can be synthesized by, for example, the method described in Japanese Unexamined Patent Publication No. 47-14127; Japanese Unexamined Patent Publication No. 47-16422; and Japanese Unexamined Patent Publication No. 48-1001. It is also possible that phosphorous oxychloride is allowed to react with a phenol derivative

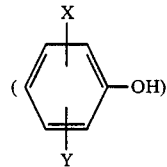

in an amount of about two times as much as phosphorus oxychloride at a temperature ranging from $-5°$ C. to $+30°$ C. for 0.5 to 3 hours and then that the reaction mixture, without isolating and purifying the compound (XIII), is used, as it is, for the condensation reaction of the compounds (XI) and (XII).

The compound (I) to be obtained by the present invention can be easily led to the compound (Ia) by, for example, a hydrolysis, elimination or catalytic reduction reaction. The hydrolysis (when $R^1$ is lower alkyl group or aralkyl group) or the elimination reactio (when $R^1$ is tert-butyl group) is conducted in water or an organic solvent such as methanol, ethanol, ethyl acetate, chloroform, tetrahydrofuran, dioxane, pyridine, acetic acid, acetone or methylene chloride, or a mixture thereof, and these reactions can also be conducted by adding an acid (e.g. hydrogen chloride, hydrogen bromide, hydrogen fluoride, hydrogen iodide, sulfuric acid, methanesulfonic acid, p-toluenesulfonic acid, trifluoroacetic acid) or a base (e.g. sodium hydroxide, potassium hydroxide, potassium carbonate, sodium hydrogen carbonate, sodium carbonate, sodium acetate). The above reaction is usually conducted at a temperature ranging from $-20°$ C. to $+150°$ C. The catalytic reduction (when $R^1$ is benzyl group) is conducted in water or an organic solvent such as methanol, ethanol, ethyl acetate, dioxane or tetrahydrofuran, or a mixture thereof in the presence of a suitable catalyst such as palladium-carbon. This reaction is conducted under a pressure ranging from atmospheric pressure to about 150 kg/cm$^2$ at a temperature ranging from $-20°$ C. to $+150°$ C.

The above-mentioned catalytic reduction is desirably conducted by using, relative to the compound (I), 1 to 100 (W/W) % (preferably 2 to 20 (W/W) % [dry basis] of palladium-carbon in a lower($C_{1-4}$)alcohol (e.g. methanol, ethanol, propanol) or a mixture of water and the above-mentioned lower alcohol, under a hydrogen pressure ranging from atmospheric pressure to 10 kg/cm$^2$ at a temperature ranging from 0° C. to $+40°$ C. The reaction period ranges from about 0.5 to about 5 hours, and it is preferable to add an acid (e.g. hydrogen chloride) to the solvent.

The salt (preferably pharmaceutically acceptable acid addition salt) of the compound (Ia) may be obtained by the reaction for producing the compound (Ia), but can also produced by addition of an acid (e.g. hydrogen chloride) to the compound (Ia).

WORKING EXAMPLES

The following Examples will illustrate the present invention, but they are not intended to limit the present invention. The purity of the products was calculated, using high performance liquid chromatography (HPLC), by comparing with an authentic sample or by the peak area percentage method. For the analysis, the following conditions were employed.

| | |
|---|---|
| Column | Nucleosil $_{10}C_{18}$ (4.0 mmID × 300 mm) |
| Mobile phase | acetonitrile/0.03M potassium dihydrogenphosphate solution = 65/35 |
| Flow rate | 1 ml/min. |
| Detection | 254 nm |

EXAMPLE 1

N-[(S)-1-Ethoxycarbonyl-3-phenylpropyl]-L-alanine [5.0 g (18 mmol.)] and tert-butyl N-(indan-2-yl)glycinate [5.5 g (22 mmol.)] were added to methylene chloride (200 ml), and the mixture was cooled with ice. Triethylamine [2.6 ml (19 mmol.)] was added to the mixture. While the reaction mixture was stirred under ice-cooling, diphenyl phosphorochloridate (commerically available) [7.2 g (27 mmol.)] was added thereto, and then a methylene chloride solution (30 ml) of triethylamine [2.6 ml (19 mmol.)] was added dropwise to the resulting mixture. The reaction mixture was stirred at 10° C. or below for two hours, and then poured into a mixture of water (400 ml) and methylene chloride (200 ml). The organic layer was separated, washed with a 10% aqueous solution of phosphoric acid (300 ml), a 1N sodium hydroxide solution (300 ml) and water (400 ml), and then dried over anhydrous magnesium sulfate. The solvent was distilled off under reduced pressure to obtain a yellow oily product (13.9 g). Quantitative determination of the desired product, tert-butyl N-[N-[(S)-1-ethoxycarbonyl-3-phenylpropyl]-L-alanyl]-N-(indan-2-yl)glycinate, in the oily product was carried out by comparing with an authentic sample by means of HPLC to find that the purity was 65.6% and the yield was 98%.

The above-mentioned oily product was dissolved in ethyl acetate (100 ml). An aqueous solution of sodium bicarbonate was added to the above solution, and the mixture was stirred at room temperature for 30 minutes. The ethyl acetate layer was separated and concentrated under reduced pressure to thereby raise the purity of the desired product up to 94%.

The authentic sample was prepared by the method described in Chem. Pharm. Bull. 34, p. 2852 (1986).

EXAMPLE 2 tert-Butyl N-(indan-2-yl)glycinate [3.54 g (14.3 mmol.)] was dissolved in methylene chloride (90 ml), and the solution was cooled to 5° C. or below. A methylene chloride solution (10 ml) of diphenyl phosphorochloridate [4.81 g (17.9 mmol.)] and triethylamine [2.5 g (25 mmol.)] were added to the above solution under stirring at the same temperature. The mixture was stirred for further 2 hours, and then allowed to stand overnight at room temperature. N-[(S)-1-Ethoxycarbonyl-3-phenylpropyl]-L-alanine [3.33 g (11.9 mmol.)] was added to the mixture, and the resulting reaction mixture was stirred at room temperature for two hours. The reaction mixture was washed with water (100 ml) and a 10% phosphoric acid solution (60 ml), and then the solvent was distilled off. The residue was dissolved in ethyl acetate (100 ml). The solution was washed with a 10% sodium carbonate solution (50 ml) and water (60 ml), and then ethyl acetate was distilled off under reduced pressure to obtain a yellow oily product (7.61 g). Quantitative determination of tert-butyl N-[N-[(S)-1-ethoxycarbonyl-3-phenylpropyl]-L-alanyl]-N-(indan-2-yl)glycinate in the oily product was carried out to find that the purity was 80% and the yield was 100%.

EXAMPLE 3

N-[(S)-1-Ethoxycarbonyl-3-phenylpropyl]-L-alanine [10.0 g (35.8 mmol.)] and ethyl N-(indan-2-yl)glycinate [9.42 g (43.0 mmol.)] were suspended in methylene chloride (250 ml), and the suspension was cooled with ice. Triethylamine [5.2 ml (37 mmol.)] was added to the suspension to make it clear. Diphenyl phosphorochloridate [8.9 ml (43 mmol.)] was added to the mixture. Then, a methylene chloride solution (25 ml) of triethylamine [5.2 ml (37 mmol.)] was added dropwise to the mixture, and the resulting mixture was stirred for 2 hours at 10° C. or below. The reaction mixture was washed with water (300 ml), a 10% phosphoric acid solution (300 ml each portion) twice and water (300 ml), and then the organic layer was concentrated under reduced pressure. The residue was dissolved in ethyl acetate (300 ml), and the solution was washed with a 10% phosphoric acid solution (300 ml), a 10% sodium carbonate solution (300 ml) and a dilute aqueous solution of sodium chloride (300 ml), successively, and then dried over anhydrous magnesium sulfate. The solvent was distilled off under reduced pressure to obtain an oil (17.12 g) in which the principal component was ethyl N-[N-[(S)-1-ethoxycarbonyl-3-phenylpropyl]-L-alanyl]-N-(indan-2-yl)glycinate. HPLC peak area percentage: 91.5%; yield: 91.1%.

NMR spectrum (CDCl$_3$) δ: 1.23, 1.26 (each 3H, t, CH$_3$×2), 1.32 (3H, d, CH$_3$), 4.12, 4.15 (each 2H, q, CH$_2$), 6.9–7.3 (9H, m, Ph).

In the NMR data, s means singlet, d doublet, t triplet, q quartet, m multiplet, Ph phenyl (the same applies to the subsequent Examples).

IR spectrum$_{max}^{Neat}$ cm$^{-1}$: 3300, 1740, 1645

EXAMPLE 4

N-[(S)-1-Ethoxycarbonyl-3-phenylpropyl]-L-alanine [8.00 g (28.6 mmol.)] and benzyl N-(indan-2-yl)glycinate [9.67 g (34.4 mmol.)] were subjected to reaction and treatment in the same manner as those described in Example 3 to yield an oil (17.04 g) in which the principal component was benzyl N-[N-[(S)-1-ethoxycarbonyl-3-phenylpropyl]-L-alanyl]-N-(indan-2-yl)glycinate. HPLC peak area percentage: 87.5%; yield: 96.0%.

NMR spectrum (CDCl$_3$) δ: (3H, t, CH$_3$), 1.33 (3H, d, CH$_3$), 4.16 (2H, q, CH$_2$), 5.07 (2H, s, CH$_2$), 7.0–7.4 (14H, m, Ph).

IR spectrum$_{max}^{Neat}$ cm$^{-1}$: 3300, 1740, 1645

EXAMPLE 5

Ethyl N-(indan-2-yl)glycinate [8.16 g (37.2 mmol.)], diphenyl phosphorochloridate [7.2 ml (34 mmol.)] and triethylamine [4.8 ml (34 mmol.)] were dissolved in methylene chloride (240 ml). The solution was stirred for 7 hours at room temperature, and then allowed to stand overnight. N-[(S)-1-Ethoxycarbonyl-3-phenylpropyl]-L-alanine [8.00 g (28.6 mmol.)] was added to the solution, and the mixture was cooled with ice. A methylene chloride solution (12 ml) of triethylamine [4.2 ml (30 mmol.] was added dropwise to the above-mentioned mixture and the resulting mixture was stirred for 2 hours at 10° C. or below. The reaction mixture was treated in the same manner as that in Example 3 to obtain an oil (13.46 g) in which the principal component was ethyl N-[N-[(S)-1-ethoxycarbonyl-3-phenylpropyl]-L-alanyl]-N-(indan-2-yl)glycinate. HPLC peak area percentage: 91.6%; yield: 89.6%.

EXAMPLE 6

Benzyl N-(indan-2-yl)glycinate [9.67 g (34.4 mmol.)], diphenyl phosphorochloridate [7.2 ml (34 mmol.)] and triethylamine [4.8 ml (34 mmol.)] were dissolved in methylene chloride (200 ml). The mixture was stirred for 6 hours at room temperature, and then allowed to stand overnight. N-[(S)-1-Ethoxycarbonyl-3-phenylpropyl]-L-alanine [8.00 g (28.6 mmol.)] was added to the reaction mixture. After ice-cooling, a methylene chloride solution (20 ml) of triethylamine [42 ml (30 mmol.)] was added dropwise to the reaction mixture. The resulting mixture was stirred for 2 hours at 10° C. or below and then treated in the same manner as that in Example 3 to obtain an oil (16.94 g) in which the principal component was benzyl N-[N-[(S)-1-ethoxycarbonyl-3-phenylpropyl]-L-alanyl]-N-(indan-2-yl)glycinate. HPLC peak area percentage: 88.7%; yield: 96.7%.

EXAMPLE 7

Phenol [10.1 g (0.107 mol)] was dissolved in methylene chloride (100 ml). The solution was cooled to 5° C. or below, and phosphorus oxychloride [8.23 g (54 mmol.)] was added to the solution. At the same temperature, a methylene chloride solution (30 ml) of triethylamine [10.9 g (0.107 mol.)] was added dropwise to the mixture, and then the resulting mixture was stirred for one hour at 10° C. or below.

On the other hand, a solution of methylene chloride (300 ml), N-[(S)-1-ethoxycarbonyl-3-phenylpropyl]-L-alanine [10.0 g (35.8 mmol.)], tert-butyl N-(indan-2-yl)glycinate [10.6 g (42.9 mmol.)] and triethylamine [3.78 g (37.3 mmol.)] was prepared. The above-mentioned diphenyl phosphorochloridate solution was added dropwise at 10° C. or below to that solution. The resulting mixture was stirred for two further hours at the same temperature. The reaction mixture was washed with water (400 ml), a 10% phophoric acid solution (300 ml) twice and water (400 ml), and then the solvent was distilled off. The residue was dissolved in ethyl acetate (150 ml). The solution was washed with a 10% phosphoric acid solution (100 ml), a 10% sodium carbonate solution (150 ml) and water (150 ml), and then concentrated to obtain the residue (20.56 g). The purity of tert-butyl N-[N-[(S)-1-ethoxycarbonyl-3-phenylpropyl]-L-alanyl]-N-(indan-2-yl)glycinate in the oily product was 82.7% and the yield was 93.4%.

EXAMPLES 8 TO 15

Under the same conditions as those in Example 7, bis-substituted-phenyl phosphorochloridate was prepared from various phenols (3 equivalents each) and phosphorus oxychloride (1.5 equivalent), and then tert-butyl N-[N-[(S)-1-ethoxycarbonyl-3-phenylpropyl]-L-alanyl]-N-(indan-2-yl)glycinate was obtained. This product was quantitatively determined by HPLC, and the yield was calculated.

| Example | Phenol | Yield (g) | Purity (%) | Yield (%) |
|---|---|---|---|---|
| 8 | o-cresol | 24.0 | 65.7 | 86.6 |
| 9 | p-cresol | 23.4 | 70.8 | 91.0 |
| 10 | o-chlorophenol | 25.2 | 67.9 | 94.0 |
| 11 | p-chlorophenol | 22.8 | 70.6 | 88.4 |
| 12 | o-methoxyphenol | 23.2 | 68.1 | 86.6 |
| 13 | p-methoxyphenol | 20.7 | 80.5 | 91.5 |
| 14 | 2,4-dimethyl-phenol | 24.4 | 67.8 | 90.6 |
| 15 | m-cresol | 21.5 | 72.4 | 85.4 |

EXAMPLE 16 m-Cresol [11.50 g (0.106 mol.)] was dissolved in methylene chloride (90 ml). Phosphorus oxychloride [7.41 g (48.3 mmol.)] was added to the solution under ice-cooling. A methylene chloride solution (10 ml) of triethylamine [10.76 g (0.106 mol.)] was added dropwise to the above-mentioned solution, and the resulting mixture was stirred for one hour. Then, tert-butyl N-(indan-2-yl)glycinate [9.56 g (38.7 mmol.)] was added to the mixture at 10° C. or below, and then, triethylamine [3.78 g (37.3 mmol.)] was added thereto. The resulting mixture was stirred at room temperature for 7 hours, and then allowed to stand overnight. On the other hand, a solution of methylene chloride (290 ml), N-[(S)-1-ethoxycarbonyl-3-phenylpropyl]-L-alanine [9.0 g (32.2 mmol.)] and triethylamine [3.40 g (33.6 mmol.)] was prepared. The above-mentioned reaction mixture was added dropwise, under ice-cooling, to the solution. The resulting mixture was stirred for 2 hours at 10° C. or below, and then subjected to the same treatment and quantitative determination as in Example 7. Yield: 21.9 g; purity: 61.8%, yield percentage: 82.7%.

EXAMPLE 17

Benzyl N-[N-[(S)-1-ethoxycarbonyl-3-phenylpropyl]-L-alanyl]-N-(indan-2-yl)glycinate [30.0 g (purity 81.1%)] obtained by the same manner as that in Example 4 was dissolved in ethanol (250 ml). 35% hydrochloric acid (9.3 g) and 5% palladium-carbon (50% wet, 5.0 g) were added to the solution. Hydrogen was introduced into the mixture at about 30° C.(about one hour). After completion of the reaction, the catalyst was filtered off, and washed with ethanol. The filtrate and the washing were then concentrated under reduced pressure. Ethyl acetate (200 ml) was added to the residue, and the mixture was again concentrated. Ethyl acetate (250 ml) was then added to the concentrate, and the mixture was cooled to 10° C. or below. The precipitating crystals were collected by filtration, washed with ethyl acetate, and then dried under reduced pressure to obtain N-[N-[(S)-1-ethoxycarbonyl-3-phenylpropyl]-L-alanyl]-N-(indan-2-yl)glycine hydrochloride [21.9 g (purity 94.7%)]. Yield: 94.3%. In the mother liquor, the desired product in an amount corresponding to 3.0% was detected.

EXAMPLE 18 tert-Butyl N-[N-[(S)-1-ethoxycarbonyl-3-phenylpropyl]-L-alanyl]-N-(indan-2-yl)glycinate [19.4 g (purity 83.6%)] was dissolved in ethyl acetate (70 ml). Under cooling at 10° C. or below, hydrogen chloride gas (17.5 g) was bubbled into the solution. The cooling bath was removed, and then the reaction mixture was stirred at room temperature for 3 hours. The reaction mixture was concentrated under reduced pressure, and ethyl acetate (70 ml) was added to the residue. The mixture was stirred for 1 hour under cooling at 10° C. or below. The preciptating crystals were collected by filtration, washed with ethyl acetate and dried under reduced pressure to obtain N-[N-[(S)-1-ethoxycarbonyl-3-phenylpropyl]-L-alanyl]-N-(indan-2-yl)glycine hydrochloride [14.7 g (purity 96.0%]. Yield: 91%.

EFFECT OF THE INVENTION

By the present invention, intermediates for producing indan derivatives having anti-hypertensive activities due to ACE inhibitory activities can be obtained safely and in a good yield, and the obtained intermediates can be easily led to the indan derivatives having anti-hypertensive activities, thus the present invention being useful as a method of preparing the indan derivatives in an industrial scale.

What is claimed is:

1. A method for producing an indan derivative of the formula (Ia):

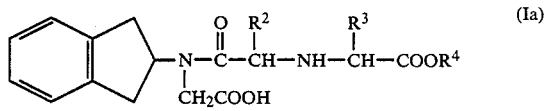

wherein $R^2$ stands for a lower alkyl group, $R^3$ stands for an aralkyl group and $R^4$ stands for a lower alkyl group, or a salt thereof, which comprises (1) allowing a diphenyl phosphorochlorodiate derivative of the formula (XIII):

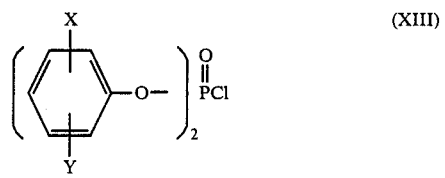

wherein X and Y independently stand for hydrogen, a lower alkyl group, a lower alkoxy group or halogen, and a compound of the formula (XII):

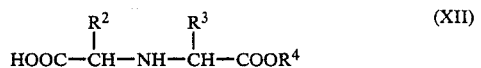

wherein $R^2$, $R^3$ and $R^4$ are of the same meaning as defined above, to react with a compound of the formula (XI):

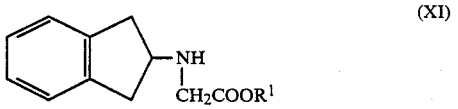

wherein $R^1$ stands for a lower alkyl group or an aralkyl group in which the phenyl moiety may have 1 to 3 members selected from the group consisting of lower alkyl, lower alkoxy and halogen, and (2) subjecting the obtained compound of the formula (I):

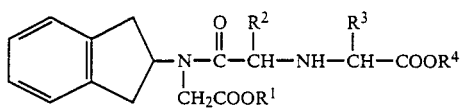 (I)

wherein each of the symbols is of the some meaning as defined above, to a hydrolysis reaction to convert $R^1$ into hydrogen, and if desired, converting the obtained compound of the formula (Ia) into a salt thereof.

2. A method according to claim 1, wherein $R^2$ stands for methyl group, $R^3$ stands for 2-phenylethyl group and $R^4$ stands for ethyl group.

3. A method according to claim 1, wherein the compound of the formula (XII) is N-[(S)-1-ethoxycarbonyl-3-phenylpropyl]-L-alanine.

4. A method according to claim 1, wherein X and Y stand for hydrogen.

5. A method according to claim 1, wherein the compound of the formula (XIII) is prepared by reacting phosphorus oxychloride and a phenol derivative of the formula:

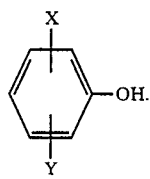

6. A method according to claim 1, wherein the reaction of the compound of the formula (XI), the compound of the formula (XII) and the compound of the formula (XIII) is conducted in the presence of a base.

7. A method according to claim 1, wherein the compound of the formula (Ia) is N-[N-[(S)-1-ethoxycarbonyl-3-phenylpropyl]-L-alanyl]-N-(indan-2-yl)glycine or a hydrochloride salt thereof.

8. A method for producing an indan derivative of the formula (I):

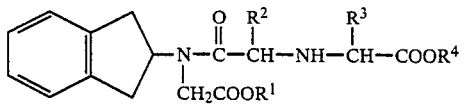 (I)

wherein $R^1$ stands for a lower alkyl group or an aralkyl group in which the phenyl moiety may have 1 to 3 members selected from the group consisting of lower alkyl, lower alkoxy and halogen, $R^2$ stands for a lower alkyl group, $R^3$ stands for an aralkyl group and $R^4$ stands for a lower alkyl group, which comprises allowing a diphenyl phosphorochloridate derivative of the formula (XIII):

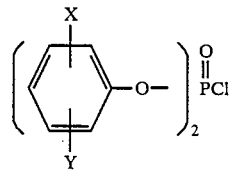 (XIII)

wherein X and Y independently stand for hydrogen, a lower alkyl group, a lower alkoxy group or halogen, and a compound of the formula (XII):

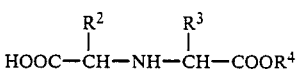 (XII)

wherein $R^2$, $R^3$ and $R^4$ are of the same meaning as defined above, to react with a compound of the formula (XI)

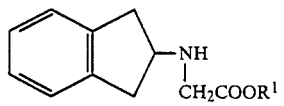 (XI)

wherein $R^1$ is of the same meaning as defined above.

9. A method according to claim 8, wherein $R^2$ stands for methyl group, $R^3$ stands for 2-phenylethyl group and $R^4$ stands for ethyl group.

10. A method according to claim 8, wherein the compound of the formula (XII) is N-[(S)-1-ethoxycarbonyl-3-phenylpropyl]-L-alanine.

11. A method according to claim 8, wherein X and Y stand for hydrogen.

12. A method according to claim 8, wherein the compound of the formula (XIII) is prepared by reacting phosphorus oxychloride and a phenol derivative of the formula:

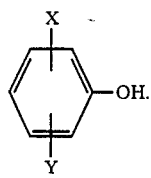

13. A method according to claim 8, wherein the reaction of the compound of the formula (XI), the compound of the formula (XII) and the compound of the formula (XIII) is conducted in the presence of a base.

14. A method for producing an indan derivative of the formula (Ia):

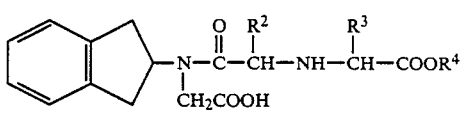 (Ia)

wherein $R^2$ stands for a lower alkyl group, $R^3$ stands for an aralkyl group and $R^4$ stands for a lower alkyl group, or a salt thereof, which comprises (1) allowing a diphenyl phosphorochloridate derivative of the formula (XIII):

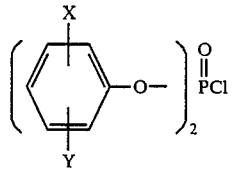 (XIII)

wherein X and Y independently stand for hydrogen, a lower alkyl group, a lower alkoxy group or halogen, and a compound of the formula (XII):

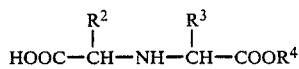 (XII)

wherein $R^2$, $R^3$ and $R^4$ are of the same meaning as defined above, to react with a compound of the formula (XI):

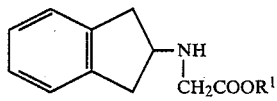 (XI)

wherein $R^1$ stands for tert-butyl group, and (2) subjecting the obtained compound of the formula (I):

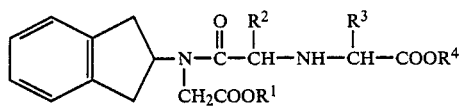 (I)

wherein each of the symbols is of the same meaning as defined above, to an elimination reaction to convert $R^1$ into hydrogen, and if desired, converting the obtained compound of the formula (Ia) into a salt thereof.

15. A method according to claim 14, wherein $R^2$ stands for methyl group, $R^3$ stands for 2-phenylethyl group and $R^4$ stands for ethyl group.

16. A method according to claim 14, wherein the compound of the formula (XII) is N-[(S)-1-ethoxycarbonyl-3-phenylpropyl]-L-alanine.

17. A method according to claim 14, wherein X and Y stand for hydrogen.

18. A method according to claim 14, wherein the compound of the formula (XIII) is prepared by reacting phosphorus oxychloride and a phenol derivative of the formula:

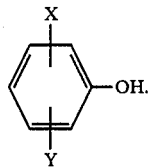

19. A method according to claim 14, wherein the reaction of the compound of the formula (XI), the compound of the formula (XII) and the compound of the formula (XIII) is conducted in the presence of a base.

20. A method according to claim 14, wherein the compound of the formula (Ia) is N-[N-[(S)-1-ethoxycarbonyl-3-phenylpropyl]-L-alanyl]-N-(indan-2-yl)glycine or a hydrochloride thereof.

21. A method according to claim 14, wherein the elimination reaction is conducted in the presence of an acid.

22. A method for producing an indan derivative of the formula (I):

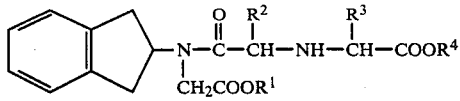 (I)

wherein $R^1$ stands for tert-butyl group, $R^2$ stands for a lower alkyl group, $R^3$ stands for an aralkyl group and $R^4$ stands for a lower alkyl group, which comprises allowing a diphenyl phosphorochloridate derivative of the formula (XIII):

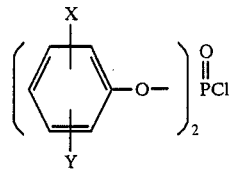 (XIII)

wherein X and Y independently stand for hydrogen, a lower alkyl group, a lower alkoxy group or halogen, and a compound of the formula (XII):

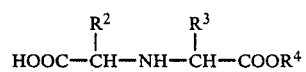 (XII)

wherein $R^2$, $R^3$ and $R^4$ are of the same meaning as defined above, to react with a compound of the formula (XI)

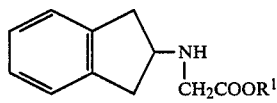 (XI)

wherein $R^1$ is of the same meaning as defined above.

23. A method according to claim 22, wherein $R^2$ stands for methyl group, $R^3$ stands for 2-phenylethyl group and $R^4$ stands for ethyl group.

24. A method according to claim 22, wherein the compound of the formula (XII) is N-[(S)-1-ethoxycarbonyl-3-phenylpropyl]-L-alanine.

25. A method according to claim 22, wherein X and Y stand for hydrogen.

26. A method according to claim 22, wherein the compound of the formula (XIII) is prepared by reacting phosphorus oxychloride and a phenol derivative of the formula:

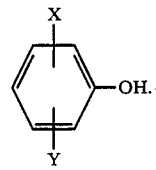

27. A method according to claim 22, wherein the reaction of the compound of the formula (XI), the compound of the formula (XII) and the compound of the formula (XIII) is conducted in the presence of a base.

28. A method for producing an indan derivative of the formula (Ia):

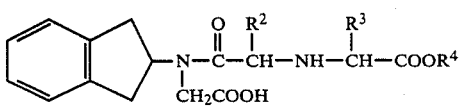 (Ia)

wherein $R^2$ stands for a lower alkyl group, $R^3$ stands for an aralkyl group and $R^4$ stands for a lower alkyl group, or a salt thereof, which comprises (1) allowing a diphenyl phosphorochloridate derivative of the formula (XIII):

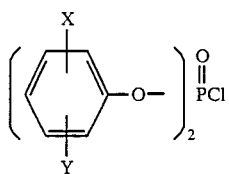

wherein X and Y independently stand for hydrogen, a lower alkyl group, a lower alkoxy group or halogen, and a compound of the formula (XII):

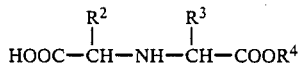

wherein $R^2$, $R^3$ and $R^4$ are of the same meaning as defined above, to react with a compound of the formula (XI):

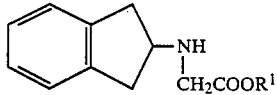

wherein $R^1$ stands for benzyl group in which the phenyl moiety may have 1 to 3 members selected from the group consisting of lower alkyl, lower alkoxy and halogen, and (2) subjecting the obtained compound of the formula (I):

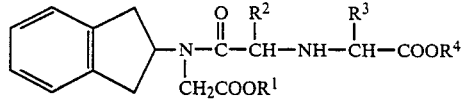

wherein each of the symbols is of the same meaning as defined above, to a catalytic reduction reaction to convert $R^1$ into hydrogen, and if desired, converting the obtained compound of the formula (Ia) into a salt thereof.

29. A method according to claim 28, wherein $R^1$ stands for benzyl group.

30. A method according to claim 28, wherein $R^2$ stands for methyl group, $R^3$ stands for 2-phenylethyl group and $R^4$ stands for ethyl group.

31. A method according to claim 28, wherein the compound of the formula (XII) is N-[(S)-1-ethoxycarbonyl-3-phenylpropyl]-L-alanine.

32. A method according to claim 28, wherein X and Y stand for hydrogen.

33. A method according to claim 28, wherein the compound of the formula (XIII) is prepared by reacting phosphorus oxychloride and a phenol derivative of the formula:

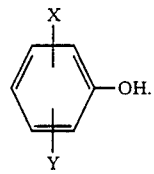

34. A method according to claim 28, wherein the reaction of the compound of the formula (XI), the compound of the formula (XII) and the compound of the formula (XIII) is conducted in the presence of a base.

35. A method according to claim 28, wherein the compound of the formula (Ia) is N-[N-[(S)-1-ethoxycarbonyl-3-phenylpropyl]-L-alanyl]-N-(indan-2-yl)glycine or a hydrochloride thereof.

36. A method according to claim 28, wherein the catalytic reduction reaction is conducted in the presence of an acid.

37. A method for producing an indan derivative of the formula (I):

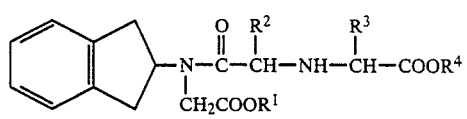

wherein $R^1$ stands for benzyl group in which the phenyl moiety may have 1 to 3 members selected from the group consisting of lower alkyl, lower alkoxy and halogen, $R^2$ stands for a lower alkyl group, $R^3$ stands for an aralkyl group and $R^4$ stands for a lower alkyl group, which comprises allowing a diphenyl phosphorochloridate derivative of the formula (XIII):

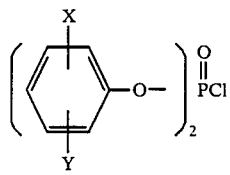

wherein X and Y independently stand for hydrogen, a lower alkyl group, a lower alkoxy group or halogen, and a compound of the formula (XII):

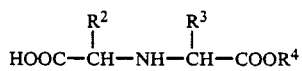

wherein $R^2$, $R^3$ and $R^4$ are of the same meaning as defined above, to react with a compound of the formula (XI):

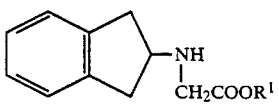

wherein $R^1$ is of the same meaing as defined above.

38. A method according to claim 37, wherein $R^1$ stands for benzyl group.

39. A method according to claim 37, wherein $R^2$ stands for methyl group, $R^3$ stands for 2-phenylethyl group and $R^4$ stands for ethyl group.

40. A method according to claim 37, wherein the compound of the formula (XII) is N-[(S)-1-ethoxycarbonyl-3-phenylpropyl]-L-alanine.

41. A method according to claim 37, wherein X and Y stand for hydrogen.

42. A method according to claim 37, wherein the compound of the formula (XIII) is prepared by reacting phosphorus oxychloride and a phenol derivative of the formula:

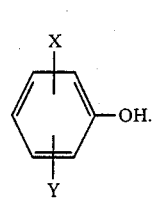

43. A method according to claim 37, wherein the reaction of the compound of the formula (XI), the compound of the formula (XII) and the compound of the formula (XIII) is conducted in the presence of a base.

44. A method according to claim 37, wherein the compound of the formula (I) is benzyl N-[N-([(S)-1-ethoxycarbonyl-3-phenylpropyl]-L-alanyl]-N-(indan-2-yl)glycinate.

* * * * *